(12) United States Patent
Lundqvist et al.

(10) Patent No.: US 6,486,137 B1
(45) Date of Patent: Nov. 26, 2002

(54) OLIGOSACCHARIDE MIXTURES HAVING ANTITHROMBOTIC ACTIVITY

(75) Inventors: Mons Lundqvist, København; Kristian Betton Johansen, Hellebæk, both of (DK)

(73) Assignee: Leo Pharmaceutical Products Ltd. A/S, Ballerup (DK)

( * ) Notice: Subject to any disclaimer, the term of this patent is extended or adjusted under 35 U.S.C. 154(b) by 0 days.

(21) Appl. No.: 09/445,146

(22) PCT Filed: May 15, 1998

(86) PCT No.: PCT/EP98/03007

§ 371 (c)(1),
(2), (4) Date: Dec. 3, 1999

(87) PCT Pub. No.: WO98/55514

PCT Pub. Date: Dec. 10, 1998

(30) Foreign Application Priority Data

Jun. 3, 1997 (GB) .............................................. 9711443

(51) Int. Cl.⁷ ........................ A61K 31/726; C08B 37/02
(52) U.S. Cl. .............................. 514/54; 536/53; 536/54
(58) Field of Search ........................ 536/53, 54; 514/54

(56) References Cited

U.S. PATENT DOCUMENTS 5,547,944 A * 8/1996 Mascellani et al. ............ 514/54
5,922,690 A * 7/1999 Van Gorp et al. ............. 514/54

FOREIGN PATENT DOCUMENTS

WO 90 04607 5/1990
WO 93 05075 3/1993

OTHER PUBLICATIONS

Tellefsen et al: "Molecular size of dermatan sulfate oligosaccharides required to bind and activate heparin confactor II", Journal of biological chemistry, vol. 261 No. 19, 1986 pp. 8854–8858, XP002078751.

Mascellani et al: "active site for heparin cofactor II in low molecular mass dermatan sulfate. Contribution to the antithrombotic activity of fractions with high affinity for heparin cofactor II", thrombosis Reasearch, vol. 84, No 1, 1996, p. 21–32, XP002079425.

* cited by examiner

*Primary Examiner*—James O. Wilson
*Assistant Examiner*—Leigh C. Maier
(74) *Attorney, Agent, or Firm*—Birch Stewart Kolasch & Birch LLP

(57) ABSTRACT

A mixture of linear oligosaccharides containing different numbers of repeating sulphated disaccharide units derived from L-iduronic acid (IdoA) and N-acetyl-D-galactosamine (Gal-NAc) and having the following characteristics (a) a molecular weight in the range of 1600–20000 for 90% or more of the mixture, (b) a sulphur content of 6.0–8.0% by weight, (c) a sulphate/carboxylate ratio of 1.2–1.6, (d) a disulphated disaccharide content of 20–60% by weight of the mono-sulphated disaccharide content, and (e) an antithrombin activity of 20–60 IU/mg. The mixture may be used as an antithrombotic agent and is prepared by depolymerisation of dermatan sulphate by periodate oxidation, followed by borohydride reduction and acid hydrolysis and then ion exchange fractionation.

7 Claims, No Drawings

OLIGOSACCHARIDE MIXTURES HAVING ANTITHROMBOTIC ACTIVITY

This application is the national phase of international application PCT/EP98/03007 filed May 15, 1998 which designated the U.S.

TECHNICAL FIELD

The invention concerns oligosaccharide mixtures having antithrombotic activity and is particularly concerned with oligosaccharides derived from dermatan sulphate.

BACKGROUND ART

Dermatan sulphate is a linear polysaccharide which has antithrombotic activity and is composed of alternating glucuronic or iduronic acid residues and N-acetylgalactosamine residues, these residues being sulphated to a varying extent. The mechanism of its activity in the inhibition of thrombin depends on the dermatan sulphate binding to both heparin cofactor II (HCII, a serine protease inhibitor) and to thrombin (factor IIa) itself.

Numerous studies have been made in the past of dermatan sulphate and its degradation products and these studies have mostly been directed to the identification and isolation of specific fragments having activity of interest. Thus for example J. Biological Chemistry, vol. 261, July 1986, 8854–58 describes fragments containing 12–14 sugar residues which bind to HCII and the same article also describes di-, tetra-, and hexasaccharide fragments without this binding ability. J. Biological Chemistry, vol. 265, October 1990, 18263–71 on the other hand describes hexasaccharides with a high binding affinity to HCII. Oligosaccharides containing 5 or 6 sugar residues and extended forms which bind to HCII are described in WO 91/15217. Thrombosis Research, 66, 1992, 527–33 suggests that the best balance of biological activity, clearance, half-life of disappearance, bioavailability, and other factors is achieved with oligosaccharides having molecular weights ranging from 4–9 kDa. WO 93/05074 describes oligosaccharides with antithrombotic activity which contain 11–13 sugar residues, and WO 93/05075 describes oligosaccharides having 7–12 sugar residues. Blood, vol. 81, April 1993, 1771–77 concludes that the fragment of minimum size for full catalytic activity is a hexadecasaccharide.

The methods used in the earlier investigations to produce the fragments studied generally involve degradation of the dermatan sulphate starting material and isolation of the fragments by affinity chromatography.

A native low molecular weight dermatan sulphate (Desmin) currently under investigation is characterised by a sulphate to carboxylate ratio of 1.06 (Thrombosis Research, vol. 83, no. 1, 103–109).

It will be appreciated from the above that numerous oligosaccharide fragments can be obtained from dermatan sulphate and the relationship between the nature of these oligosaccharides and their activity is complex and has not yet been completely elucidated.

DISCLOSURE OF THE INVENTION

We have now found that a satisfactory level of antithrombotic activity can be found in fractions which have been separated from material with a lower charge density and contain mixtures of oligosaccharides based on specific disaccharide residues.

The oligosaccharides of the invention are different from prior art since they are more negatively charged. They can be prepared by methods which are commercially more competitive compared to those previously used and described in the prior art proposals in the isolation of specific fragments, since they are less expensive to manufacture. These dermatan sulphate fractions show surprisingly higher affinity towards HQII than native dermatan sulphate and can therefore be used to increase the antithrombotic potency of dermatan sulphate based drugs.

The invention thus provides a mixture of linear oligosaccharides containing different numbers of repeating sulphated disaccharide units derived from L-iduronic acid (IdoA) and N-acetyl-D-galactosamine (Gal-NAc) and having the following characteristics:

(a) a molecular weight in the range of 1600–20000 for 90% or more of the mixture, (b) a sulphur content of 6.0–8.0% by weight, (c) a sulphate/carboxylate ratio of 1.2–1.6, (d) a disulphated disaccharide content of 20–60% by weight of the mono-sulphated disaccharide content, and (e) an antithrombin activity of 20–60 IU/mg.

The mixture is prepared from dermatan sulphate and may thus contain a small proportion of residues derived from D-glucuronic acid, although it is preferably free or essentially free of such residues. Residues of hexosamines other than Gal-NAc may also be present in a small amount, e.g. residues of N-acetyl-D-glucosamine (Glu-NAc) although Gal-NAc is preferably the only hexosamine present.

The Gal-NAc residues are sulphated at the 4-position in most cases and the IdoA residues are sulphated at the 2-position in some instances. Some cases of sulphation at the 6-position of Gal-NAc are also seen. The sul-phate:carboxyl and disulphated:monosulphated disaccharide ratios and the sulphur content can thus vary, mostly depending on the extent of sulphation of the IdoA residues.

Formula 1 shows the sequence of repeating sulphated L-iduronic acid and N-acetyl-D-galactosamine units generally present in the oligosaccharides of the invention.

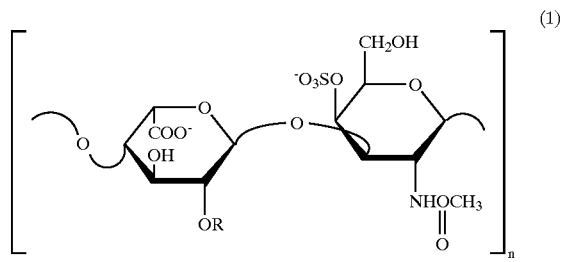

where R is H or $SO^{3-}_3$, and n is in the range 3–37 for 90% or more of the material and 10–15 for the peak point of the molecular distribution.

The residues are linked from the IdoA 1-position to the Gal-NAc 3-position and from the Gal-NAc 1-position to the IdoA 4-position. When prepared by the method described below, a proportion of the terminal Gal-NAc residues have a 2,3,4-trihydroxybutyric acid residue ($HOCH_2$—CH(O—)—CH(OH)COO$^-$) at the 1-position. The counterion is a mono- or divalent cation, mostly sodium but possibly also other ions such as calcium.

MODES OF CARRYING OUT THE INVENTION

The properties characteristic of the oligosaccharides may be measured by the following methods:

(1) molecular weight by gel permeation chromatography (GPC)—HPLC according to the method of Dedem & Nielsen, Pharmeuropa Vol. 3, No. 3, 202–218 (1991), (2) sulphur content according to Ph. Eur. V.3.5.3, (3) sulphate/carboxyl ratio according to Ph. Eur. p. 828, (4) disulphated/monosulphated disaccharide content by the method of Linhardt et al., Anal. Biochem. 181, 288–296 (1989).

(5) HCII-mediated antithrombin activity by a chromogenic assay (Diagnostica Stago, France) in a plasma free system with the 4. International Heparin Standard (code no. 82/502) as standard.

The sulphur content of the mixtures is generally within the range 6.0–8.0% by weight and is preferably 6.5–8.0%. The sulphate/carboxyl ratio can generally range from 1.2–1.6 and is preferably from 1.3–1.6. The content of disulphated disaccharide is usually from 20–60% by weight of the monosulphated disaccharide content and is preferably 30–60% of the latter. The HCII mediated antithrombin activity of the oligosaccharides of the invention is generally in the range 20–60 IU/mg and preferably 30–60 IU/mg.

The oligosaccharide mixture of the invention may be prepared by depolymerisation of dermatan sulphate by periodate oxidation, followed by borohydride reduction and acid hydrolysis and then ion exchange fractionation.

The dermatan sulphate used as the starting material may be derived from animal intestines such as for example porcine mucosa or bovine trachea and have the following characteristics:

Specific optical rotation (4% in water): −50° to −70°

Sulphur: 5.3–6.3% (w/w)

Sulphate/carboxylate ratio: 1.0–1.3

HCII mediated antithrombin activity: 2–10 IU/mg

The main chemical reactions involved in the depolymerisation process are shown in the reaction scheme below and principally follow the route described in Carbohydrate Research 36, 339–348 (1974).

Depolymerisation of dermatan sulphate:

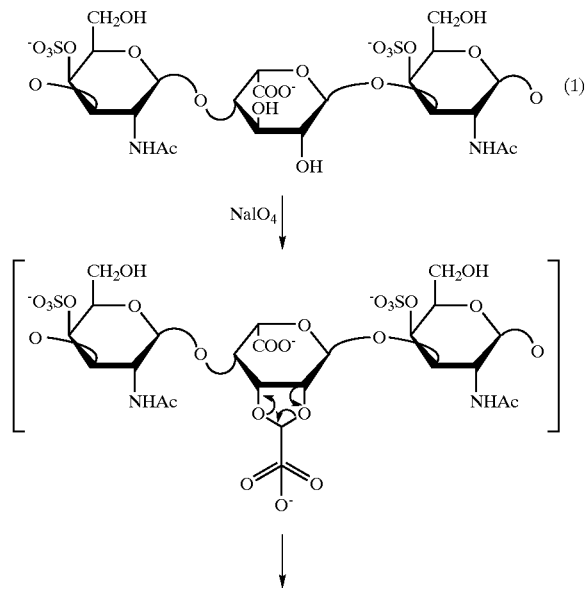

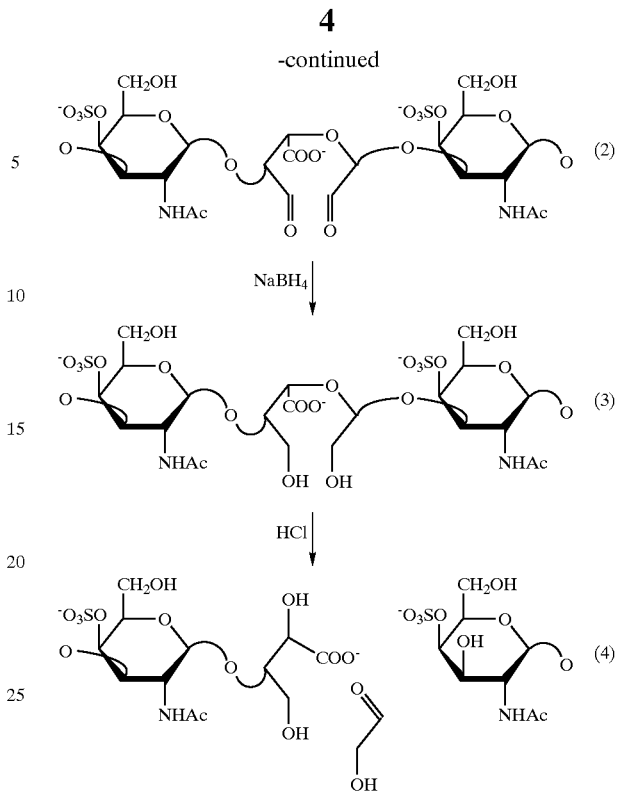

In the first step, treatment of a dermatan sulphate (1) with periodate results in selective oxidation of non-sulphated IdoA residues to produce a ring-opened dialdehyde (2). Reduction of the latter gives the diol (3) which is then cleaved by acid hydrolysis to give two Gal-NAc-terminated fragments, one of which carries a 2,3,4-trihydroxybutyric acid end group. This cleaving occurs at numerous positions along the dermatan sulphate chain, and gives a mixture of fragments of different chain lengths. A selected fraction of these fragments is then obtained by ion exchange fractionation.

The initial oxidation step may be carried out with periodic acid or a salt thereof, for example the sodium salt, in an aqueous medium at a temperature of 0–30° C. and a pH of 5–8. The reduction step may be carried out with a borohydride such as potassium or, preferably, sodium borohydride, in an aqueous medium at a temperature of 0–30° C. and a pH of 6–9. The acid hydrolysis step is preferably carried out with a mineral acid such as hydrochloric or sulphuric acid at any suitable temperature, e.g. 20–60° C.

The ion exchange fractionation of the mixture generally separates relatively highly sulphated fragments from fragments having a lower degree of sulphation, where the highly sulphated fractions are characterised by (a) a molecular weight in the range of 1600–20000 for 90% or more of the mixture, (b) a sulphur content of 6.0–8.0% by weight, (c) a sulphate/carboxylate ratio of 1.2–1.6, (d) a disulphated disaccharide content of 20–60% by weight of the mono-sulphated disaccharide content, and (e) an antithrombin activity of 20–60 IU/mg.

The fractionation may be carried out by stepwise elution using an ion exchange resin such as Amberlite IRA 404, Amberlite IRA 900, Amberlite IRA 904, Amberlite IRA 958, Amberlite IRA 67, Amberlite IRA 68, Lewatit S5428A, Lewatit S6328A, Lewatit S6328, Lewatit MP 500WS, Dowex 11, Dowex Monosphere 550A, Dowex MSA1, or any other anion exchanger.

The ion exchange step may be carried out by binding a solution of the starting material to the resin and subsequently eluting fractions with different activity from the resin depending on the ionic strength of the elution solution. Low sulphated low molecular weight products are usually eluted first and discarded, and the required highly sulphated low molecular weight material is then obtained by further elution.

The oligosaccharide mixtures of the invention can be formulated as pharmaceutical compositions for use in human or veterinary medicine as antithrombotic agents in any convenient way. Such compositions will usually include one or more acceptable carriers and may for example be in a form suitable for parenteral, oral, or topical use.

The mixtures may be formulated for use in veterinary or human medicine by injection and may be presented in unit dose form, e.g. in ampoules. The compositions for injection may be in the form of suspensions, solutions, or emulsions,. in oily or aqueous vehicles, and may contain formulatory agents such as suspending, stabilising, solubilising, and/or dispersing agents.

The compositions may also be in a form suitable for oral administration, for example in the form of solutions, syrups, or suspensions, or a dry powder for constitution with water or other suitable vehicle before use. Solid compositions such as tablets, capsules, lozenges, pills, boluses, powder, pastes, granules, bullets, or premix preparations may also be used.

The composition may also be in a form suitable for topical administration, for use in veterinary and human medicine, e.g. ointments, creams, lotions, shampoos, powders, sprays, dips, or aerosols.

The mixtures of the invention may be administered in combination with other pharmaceutically active ingredients.

The total daily dosage of mixtures of the invention employed in both veterinary and human medicine will suitably be in the range of 1–100 mg/kg bodyweight, preferably from 3–30 mg/kg and these may be given in divided doses, e.g. 1–4 times per day.

Formulations of the invention can be used for treatment of different thrombotic conditions such as deep venous thrombosis (DVT) and stroke as well as for prophylaxis in general surgery, for example hip replacements and knee operations to prevent thrombotic complications.

The following examples illustrate the invention:

EXAMPLE 1

300 g dermatan sulphate sodium isolated from porcine intestinal mucosa was dissolved in 3 l of 1% (w/v) sodium chloride solution and 17.4 g $NaIO_4$ was slowly added to the solution while stirring. The solution was stirred in the dark overnight. Then 6 g $NaBH_4$ was added carefully to the solution. After three hours at room temperature pH was adjusted to 2.0 with hydrochloric acid and the solution was stirred at 60° C. for three hours. Subsequently the pH was adjusted to 5.5 with sodium hydroxide, and the solution was filtered and precipitated with 1.7 volumes of absolute ethanol. The product had the following characteristics:

Specific optical rotation (4% in water): −55°

Sulphur: 6.3% (w/w)

Sulphate/carboxylate ratio: nd

HCII mediated antithrombin activity: 7.5 IU/mg 4.0 g of the above isolated low molecular weight dermatan sulphate was dissolved in 200 ml 0.5 M sodium chloride solution and subsequently 200 g Amberlite IRA 904 ion exchange material was added to the solution. After stirring for one hour at 60° C. pH and sodium chloride concentration was measured and adjusted to 5.8–6.0 and 0.5 (0.48–0.52) M respectively. The solution was stirred at 60° C. overnight. The ion exchange material was drained, the solution discarded, and then the material was eluted twice for low sulphated low molecular weight dermatan sulphate with 200 ml 1.2 M sodium chloride solution at 60° C., pH 5.8–6.0 while stirring overnight. After careful draining of the ion exchanger highly sulphated low molecular weight dermatan sulphate was eluted by elution twice with 200 ml 1.6 M sodium chloride solution at 60° C., pH 5.8–6.0 while stirring overnight. The pooled eluates were filtered and precipitated with 1.7 volumes of absolute ethanol. A second precipitation was performed to remove salt from the precipitate which finally yielded 0.7 g of highly sulphated low molecular weight dermatan sulphate with the following characteristics:

Peak molecular weight (Mp): 6926 Da

Sulphur: 6.9% (w/w)

Sulphate/carboxylate ratio: nd

Disulphated disaccharide content: nd

HCII mediated antithrombin activity: 36.6 IU/mg

The substance showed an $ED_{50}$ of 0.753 mg/kg in a rabbit venous thrombus model performed in the jugular veins of Mol. Russian rabbits of both sexes (body weight 2–2.5 kg) treated with 5 mg/kg thrombokinase.

EXAMPLE 2

4.0 g of low molecular weight dermatan sulphate prepared according to example 1 was bound to Amberlite IRA 904 according to example 1 and eluted twice for low sulphated low molecular weight dermatan sulphate with 1.0 M sodium chloride solution at 60° C., pH 5.8–6.0 while stirring overnight. The subsequently isolated highly sulphated low molecular weight dermatan sulphate was eluted according to example 1 and showed the following characteristics:

Peak molecular weight ($M_p$): 7170 Da

Sulphur: 7.0% (w/w)

Sulphate/carboxylate ratio: nd Di sulphated disaccharide content: nd

HCII mediated antithrombin activity: 30.9 IU/mg

EXAMPLE 3

13.0 kg dermatan sulphate sodium isolated from porcine intestinal mucosa was dissolved in 130 l of deionized water and 617 g $NaIO_4$ was slowly added to the reactor while stirring. The solution was stirred in the dark overnight. Then 260 g $NaBH_4$ was added carefully to the solution. After three hours at room temperature pH was adjusted to 2.0 with hydrochloric acid and the solution was stirred at 60° C. for six hours. Subsequently the pH was adjusted to 5.7 with sodium hydroxide and the solution was precipitated with 1.7 volumes of absolute ethanol. The yield was 2.2 kg of a product with the following characteristics:

Specific optical rotation: −53.5°

Sulphur: 5.7% (w/w)

Sulphate/carboxylate ratio: 1.3

HCII mediated antithrombin activity: 6.1 IU/mg

The above isolated low molecular weight dermatan sulphate was dissolved in 122 l 0.5 M sodium chloride solution and subsequently 4.9 kg Amberlite IRA 68 ion exchange material was added to the solution. The solution was stirred at 60° C. overnight. The ion exchange material was drained, the solution discarded, and then the material was eluated twice with 80 l 2.0 M sodium. chloride solution at 60° C., pH 6.0, overnight. The pooled eluates were precipitated twice with 1.5 volumes of absolute ethanol, filtered with 6.0 μm and spray dried from water solution. The yield was 713 g of highly sulphated low molecular weight dermatan sulphate (LMWDS) with the following characteristics:

Peak molecular weight: 5000 Da

Sulphur: 7.3% (w/w)

Sulphate/carboxylate ratio: 1.4

Disulphated disaccharide content: 39%

HCII mediated antithrombin activity 44.5 IU/mg

The LMWDS showed an $ED_{50}$ of 3.4 mg/kg 3 hours after s.c. injection in a venous thrombus model performed in the jugular veins of Mol. Russian rabbits of both sexes (body weight 2–2.5 kg) treated with 5 mg/kg thrombokinase.

The effect of the LMWDS was also studied immediately after i.v. injection in a similar jugular vein thrombosis model conducted at three dose levels in groups of 15 rabbits. The following results were obtained:

| Dose (mg/kg) | % animals showing no thrombosis |
| --- | --- |
| 1 | 12 |
| 3 | 67 |
| 10 | 80 |

What is claimed is:

1. A mixture of linear oligosaccharides prepared from dermatan sulphate, said mixture containing dermatan sulphate fragments of different chain lengths containing different numbers of repeating sulphated L-iduronic acid (IdoA) and N-acetyl-D-galactosamine (Gal-Nac) units according to the formula 1:

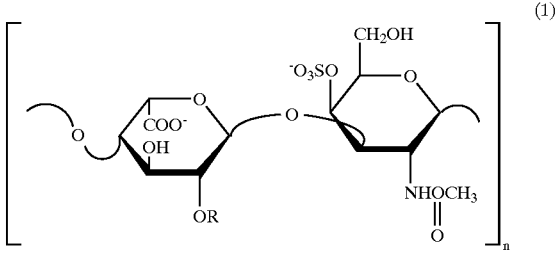

wherein R is H or $SO_3^-$, and n is the range 3–37 for 90% or more of the mixture and 10–15 for peak point of molecular weight distribution,
said mixture having the following characteristics:
   (a) a molecular weight in the range of 1600–20000 for 90% of the mixture,
   (b) a sulphur content of 6.0–8.0% by weight
   (c) a sulphate/carboxylate ratio of 1.2–1.6,
   (d) a disulphated disaccharide content of 20–60% by weight of the mono-sulphated disaccharide content, and
   (e) a heparin cofactor II mediated antithrombin activity of 20–60 IU/mg.

2. A mixture according to claim 1 which has a sulphur content of 6.5–8.0% by weight, a sulphate/carboxylate ratio of 1.3–1.6, a disulphated disaccharide content of 30–60% and an antithrombin activity of 30–60 IU/mg.

3. A mixture according to claim 1 being essentially free of D-glucuronic acid residues.

4. A mixture according to claim 1 wherein Gal-NAc is the only hexosamine present.

5. A mixture according to claim 1 wherein a proportion of the terminal Gal-NAc residues have a 2,3,4-trihydroxybutyric acid residue at the 1-position.

6. A pharmaceutical composition containing a mixture according to claim 1 and one or more carriers.

7. A pharmaceutical composition according to claim 6 formulated for injection in the form of a suspension, a solution, or an emulsion in an oily or aqueous vehicle which may contain suspending, stabilizing, solubilizing, and/or dispersing agents.

* * * * *